(12) United States Patent
Racicot et al.

(10) Patent No.: US 8,431,176 B2
(45) Date of Patent: Apr. 30, 2013

(54) LIQUID CHROMATOGRAPHIC FRACTION OF ENZYMATICALLY POLYMERIZED FLAVONOID AS AN ANTIOXIDANT

(75) Inventors: Kenneth Racicot, Hopedale, MA (US); Nicole Favreau, Waltham, MA (US); Ferdinando Bruno, Andover, MA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 414 days.

(21) Appl. No.: 12/641,368

(22) Filed: Mar. 8, 2010

(65) Prior Publication Data
US 2011/0218252 A1    Sep. 8, 2011

(51) Int. Cl.
*A23L 3/3481*    (2006.01)

(52) U.S. Cl.
USPC ........................................... 426/442

(58) Field of Classification Search .................. 426/442; 525/328.5
See application file for complete search history.

(56) References Cited

U.S. PATENT DOCUMENTS

| 8,143,308 B2 * | 3/2012 | Bruno et al. | 514/456 |
| 2007/0075020 A1 * | 4/2007 | Kelm et al. | 210/635 |
| 2011/0172389 A1 | 7/2011 | Favreau | |

FOREIGN PATENT DOCUMENTS

WO    WO 2006116532 A2 *    11/2006

* cited by examiner

*Primary Examiner* — Yong Chu
(74) *Attorney, Agent, or Firm* — Roger C. Phillips

(57) ABSTRACT

Disclosed is a separated fraction of a reaction product of an enzymatically catalyzed polymerization of a flavonoid. The separated fraction is highly resistant to oxidation and is useful in numerous applications such as an antioxidant in food products and medical applications.

3 Claims, 12 Drawing Sheets

LIQUID CHROMATOGRAPHIC FRACTION OF ENZYMATICALLY POLYMERIZED FLAVONOID AS AN ANTIOXIDANT

CROSS REFERENCE TO RELATED APPLICATION

This application is a continuation in part of U.S. Patent Application entitled "SYNTHESIS OF WATER SOLUBLE OLIGO/POLY(CATECHINS) AND METHODS OF USE", U.S. Ser. No. 11/978,540, now U.S. Pat. No. 8,143,308 the entire contents of which is hereby incorporated herein by reference.

BACKGROUND OF THE INVENTION

The present invention relates generally to the separation and/or purification of an enzymatic polyflavonoid with or without a template such as PEO (polyethylene oxide), SPS (sulfonated polystyrene) DBSA (sodium dodecyl benzene sulfonic acid), one or more of the recovered highly pure fractions and the use of one or more fractions. One or more of the recovered fractions can be used as a food antioxidant and/or a medicinal agent such as a drug.

Phenolic polymers, in particular phenol-formaldehyde resins such as novolaks and resols find wide application as wood composite laminates, foundry resins, abrasives, friction and molding materials, coatings and adhesives, fiber bonders and flame retardants. There has been a major concern however over the toxic effects of formaldehyde which are used in current art synthetic processes. In recent years there has been an effort towards the development of an alternative synthetic route which circumvents the toxic effects of formaldehyde. These synthetic routes are also not suitable for forming polymers that must be biocompatible for uses such as food additives.

Enzymatic polymerization of phenol in aqueous solutions has been initially investigated as a possible benign and environmentally friendly solution to the synthesis of polyphenols. These initial attempts however were unsuccessful since they could form only very low molecular weight (oligomers) exhibiting properties insufficient to meet the requirements for engineering applications. Alternative enzymatic reactions have since been investigated to improve molecular weight and the mechanical, thermal, optical and electronic properties of these polymers including micelles, air-water interface monolayers and mixture of various organic solvents. Although the resulting molecular weights and properties of these polyphenols were improved, their commercial application remains limited due to extensive branching and poor solubility and processability of the resulting polymers.

Recently a patent publication by Bruno et al. addresses these problematic issues and results in a new class of polyelectrolyte/polycatechin complexes which are prepared in aqueous medium using an environmentally safe, inexpensive, and facile "one-step" reaction. In addition, these polycatechins are water soluble with improved properties including molecular weight, structural, thermal, antioxidant properties and processability than current synthetic routes. Moreover, the polycatechin were found to exhibit antitumorigenic activity in in vitro studies. Flavonoids are also known to be strong antioxidants and are presently tested as food stabilizers.

However the industrial application of these polymers is hindered by the difficulties in separating the different polymers that are formed in the enzymatic polymerization. The control of structural complexity through controlled polymerization is a technical hurdle. There are 7 possible reaction sites for each flavonoid monomer resulting in 28 possible combinations for the formation of a simple dimer. The possible tetramer structures, formed by two dimers, are 107. Moreover, the procedure for the separation of the different pure fractions is challenging. The structures created from the reaction can be very similar and consequently difficult to separate.

SUMMARY OF THE INVENTION

This invention is a significant advancement over current strategies used for the analysis/separation of water soluble and processable form synthetic polyflavonoids. The present invention addresses and resolves all of the current limitations, which have prevented the commercial viability of use of enzymatically prepared poly/oligoflavonoid. The separation approach described in this invention provides a specific, analytical approach, which may be carried out at near neutral pH's. In this particular invention, polyepicatechin was optimized by carrying out the separation with an HPLC technique. This is a significant advancement in that scale-up is much more feasible since there is the separation of the different fractions. In addition, the polyflavonoid obtained from the separation, can be redissolved in ethanol with high purity, and may be easily redissolved in water. This is a significant advancement for the development of new phenolic polymers with enhanced purity and high specific antioxidant properties. The present invention affords extensive opportunities for the use of the new polyphenols in a wide variety of industrial, medical, food, electronic and optical applications.

It is an object of the present invention to provide a novel procedure for the separation of a water soluble complex and processable polyflavonoid.

It is an object of the present invention to provide a novel use for a water soluble complex and processable polyflavonoid.

It is another object of the present invention to provide a process which results in the production of a polyflavonoid of high purity which has enhanced molecular weight, thermal, mechanical, antioxidant and optical properties over the monomeric flavonoids.

It is another object of the present invention to provide a process which results in the production of a polyflavonoid of high purity which has enhanced molecular weight, thermal, mechanical, antioxidant and optical properties over the monomeric flavanoids.

It is yet another object of the present invention to provide a process which results in the separation of a polyflavonoid natural polymer complex such as polyepicatechin.

It is yet another object of the present invention to provide a process which results in the use of a polyflavonoid natural polymer complex such as a fraction polyepicatechin.

It is yet another object of the present invention to provide a process which results in the separation of a polyflavonoid natural polymer complex such as poly(−±)catechin.

It is still another object of the present invention to provide a process which results in the use of a fraction of polyflavonoids natural polymer complex such as poly(−±)catechin.

It is yet another object of the present invention to provide a process which results in the separation of a polyflavonoid natural polymer complex such as poly(−)catechin.

It is yet another object of the present invention to provide a process which results in the use of a fraction of polyflavonoids natural polymer complex such as poly(−)catechin.

It is yet another object of the present invention to provide a process which results in the separation of these polyflavonoids into various architectures including but not limited to gels, coatings, paints, micelles, reversed micelles, thin films, fibers, chaff materials, electrostatic sprays medical drugs and membranes.

It is yet another object of the present invention to provide one or more fractions of these polyflavonoids useful in various architectures including but not limited to gels, coatings, paints, micelles, reversed micelles, thin films, fibers, chaff materials, electrostatic sprays medical drugs and membranes.

It is yet another object of the present invention to provide a process which results in the separation of polyflavonoid natural polymers which may be used for applications including but not limited to food preservatives, anticancer drugs, wood composite laminates, foundry resins, abrasives, friction and molding materials, coatings and adhesives, flame retardants, smart windows, and drug delivery systems.

It is yet another object of the present invention to provide one or more fractions of polyflavonoid natural polymers which may be used for applications including but not limited to food preservatives, anticancer drugs, wood composite laminates, foundry resins, abrasives, friction and molding materials, coatings and adhesives, flame retardants, smart windows, and drug delivery systems.

It is still another object of the present invention to provide a process which results in the separation of a polyflavonoid/polyelectrolyte polymer complex where the optical and electronic properties of the final complex can be tailored and optimized by judicious choice or modification of the polyelectrolyte matrix material.

It is another object of the present invention to provide a process which results in the in the use of HPLC fractions of a polyflavonoid/polyelectrolyte polymer complex where the optical and electronic properties of the final complex can be tailored and optimized by judicious choice or modification of the polyelectrolyte matrix material.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

The present invention is in one or more separated or purified fractions of the product of an enzymatic polymerization which exhibits improved antioxidant properties, a method of separation of a reaction mixture resulting from the enzymatic polymerization of a flavonoid into two or more fractions, and the use of a separated fraction as an antioxidant. The enzymatic polymerization of flavonoids is disclosed by Bruno et al. in U.S. Patent Publication No. 2009/0170928, the disclosure of which is hereby incorporated by reference.

Figure 1:
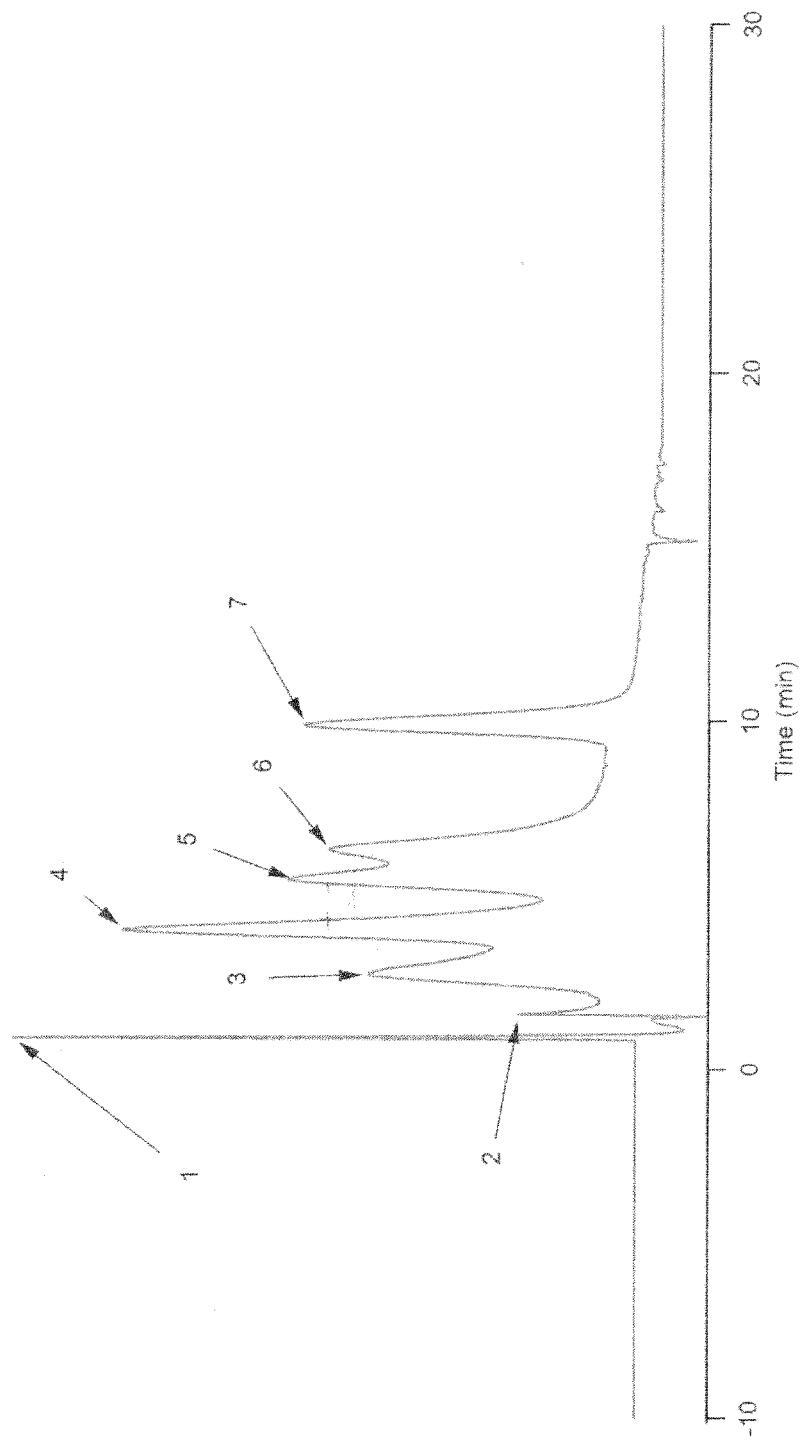
FIG. 1 shows an HPLC chromatogram of a polyepicatechin synthesized via horseradish peroxidase.
Figure 2:
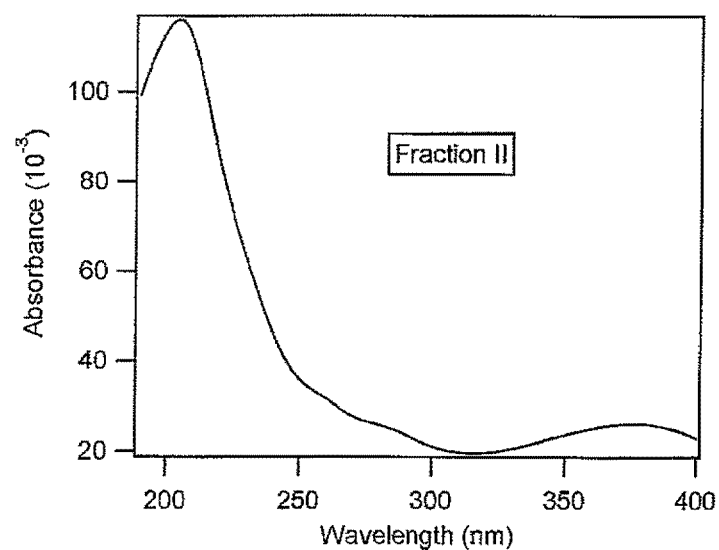
FIG. 2 shows UV-Vis spectra for factions II and III.
Figure 2:
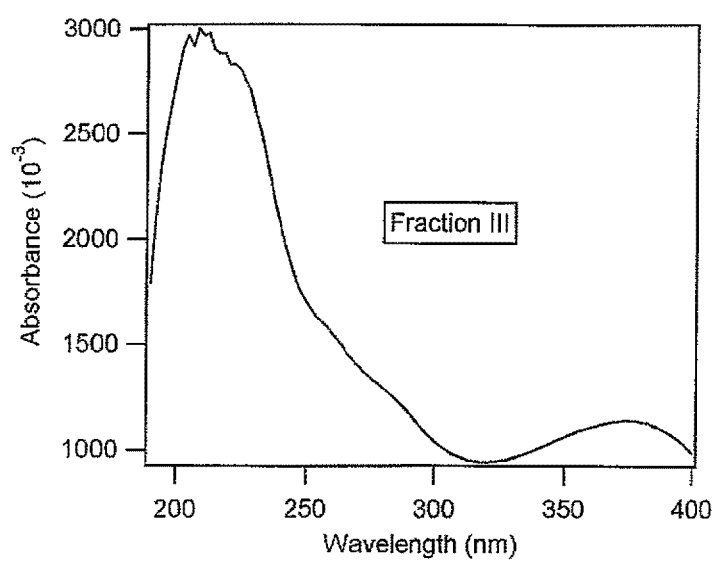
Figure 3:
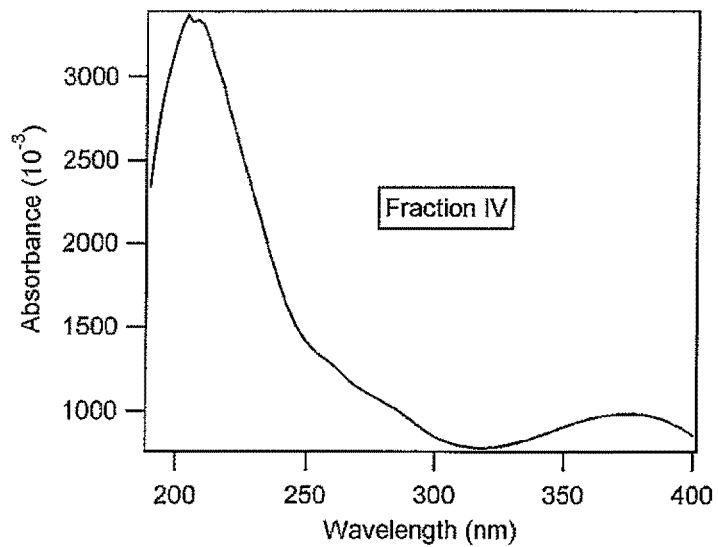
FIG. 3 shows UV-Vis spectra for fractions IV and V.
Figure 3:
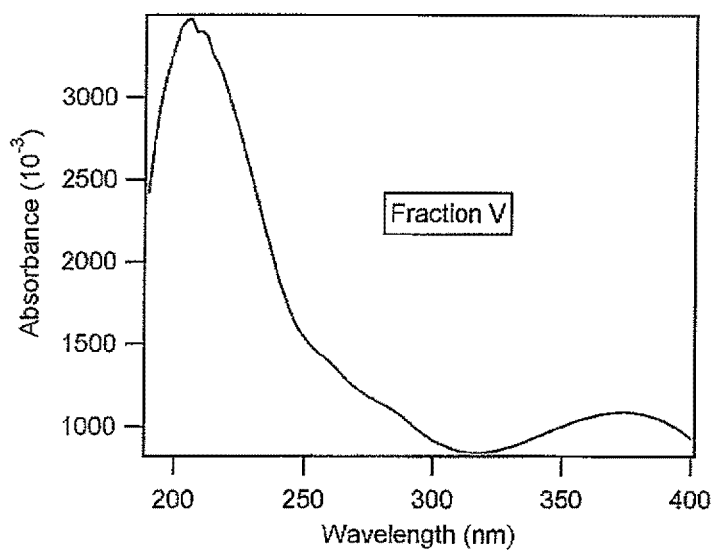
Figure 4:
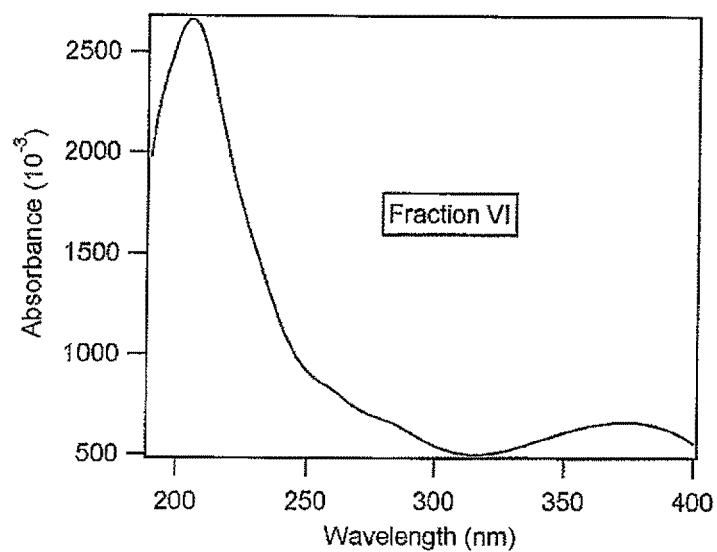
FIG. 4 shows UV-Vis spectra for fractions VI and VII.
Figure 4:
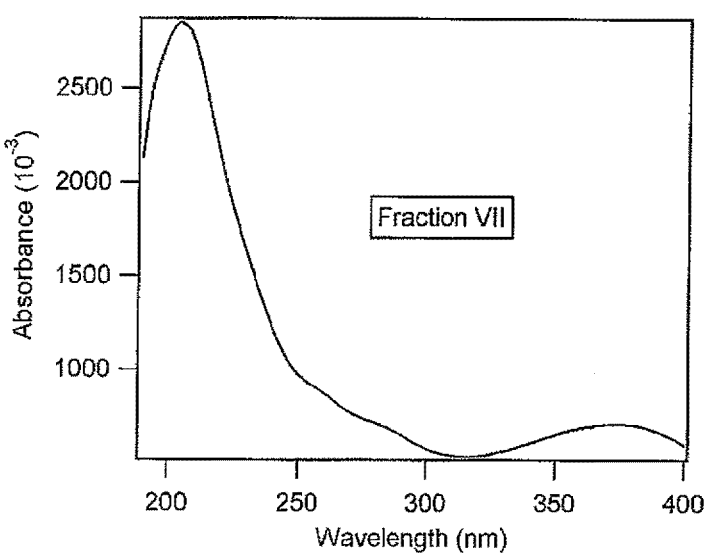
Figure 5:
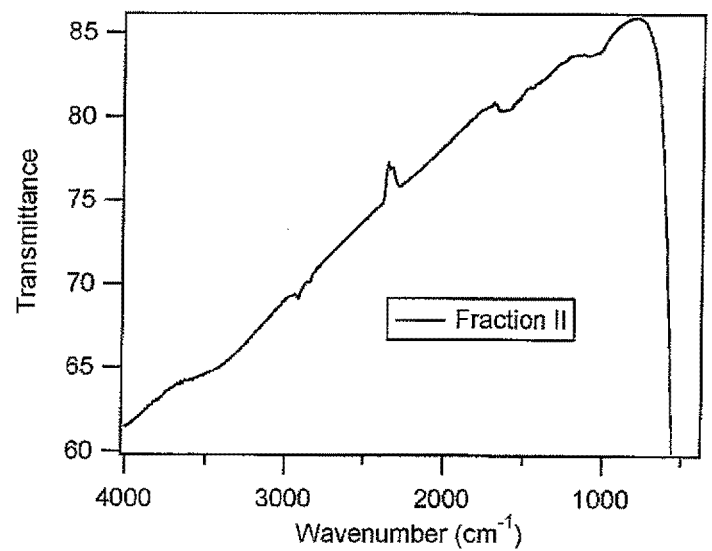
FIG. 5 shows FTIR traces for fractions II and III.
Figure 5:
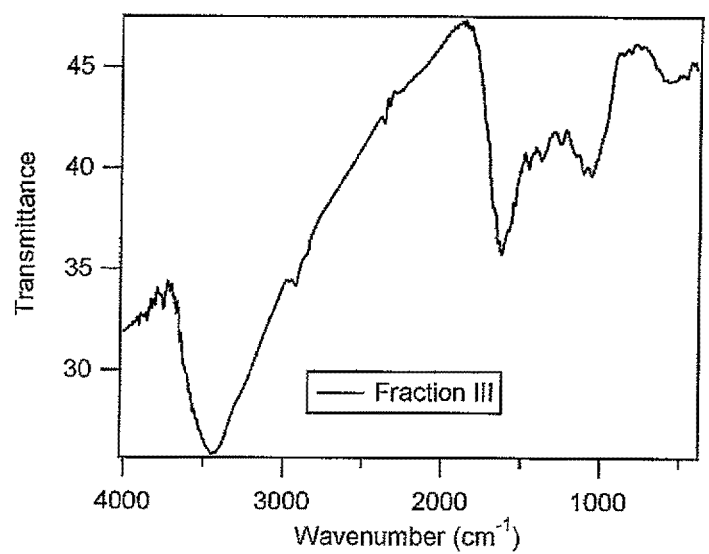
Figure 6:
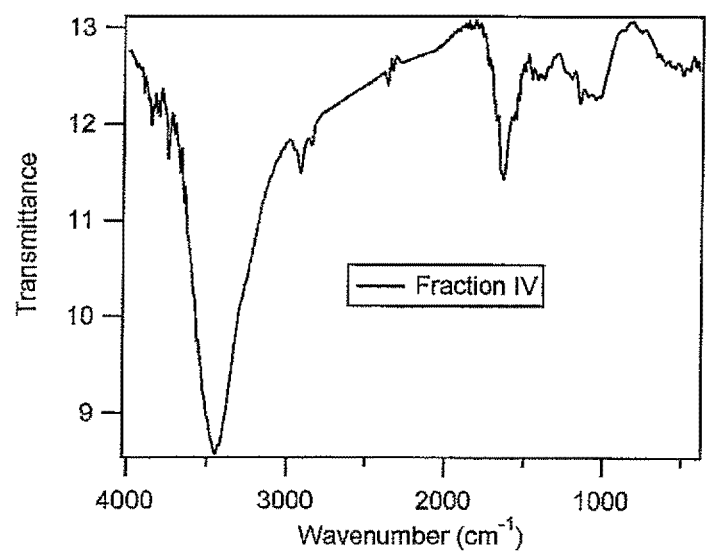
FIG. 6 shows FTIR traces for fractions IV and V.
Figure 6:
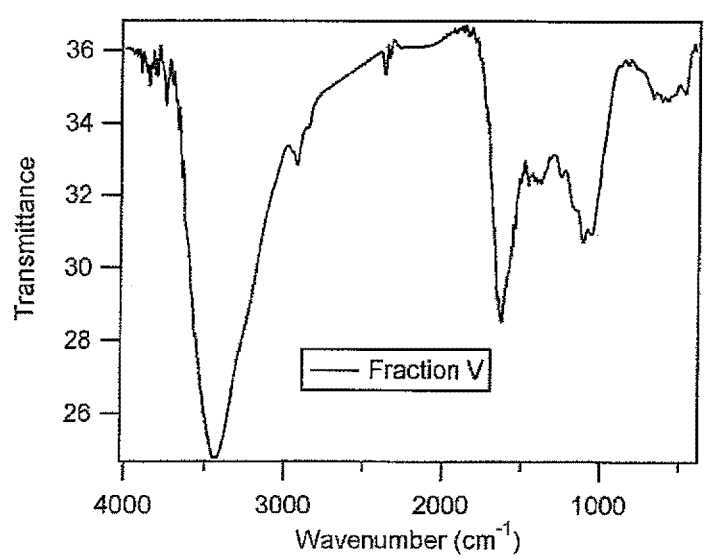
Figure 7:
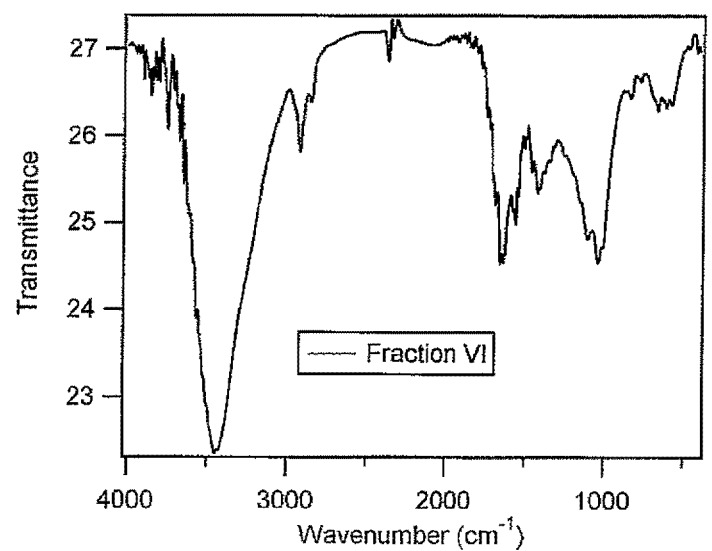
FIG. 7 shows FTIR traces for fractions VI and VII.
Figure 7:
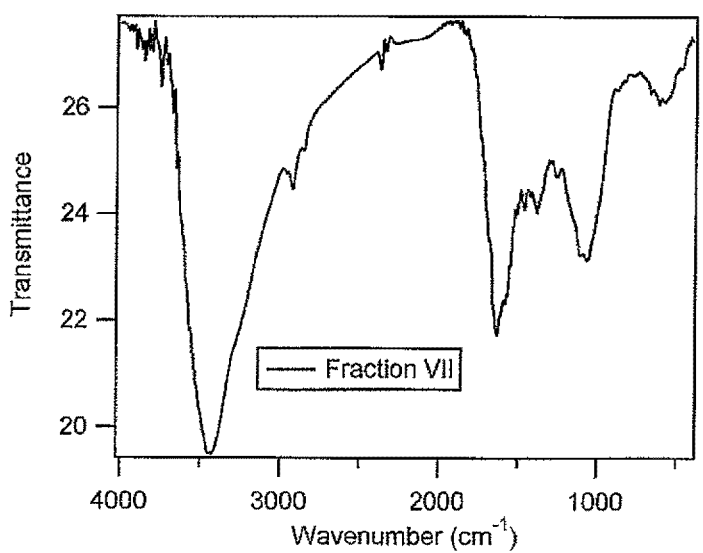
Figure 8:
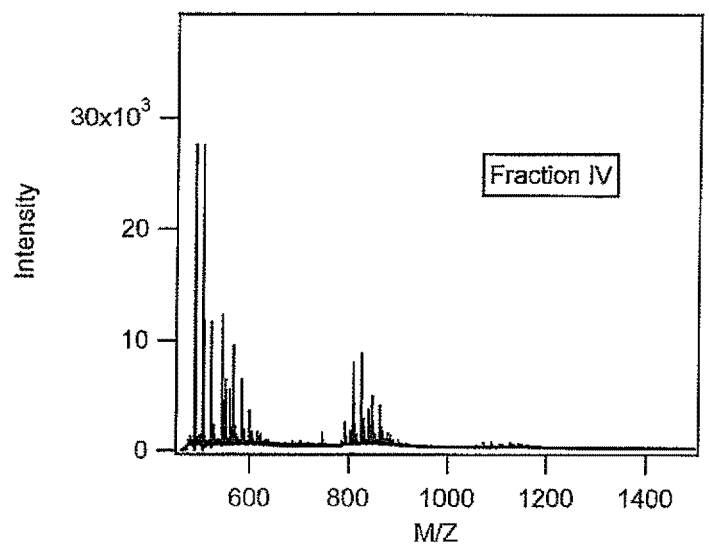
FIG. 8 shows MALDI-TOF spectra for fractions IV and V.
Figure 8:
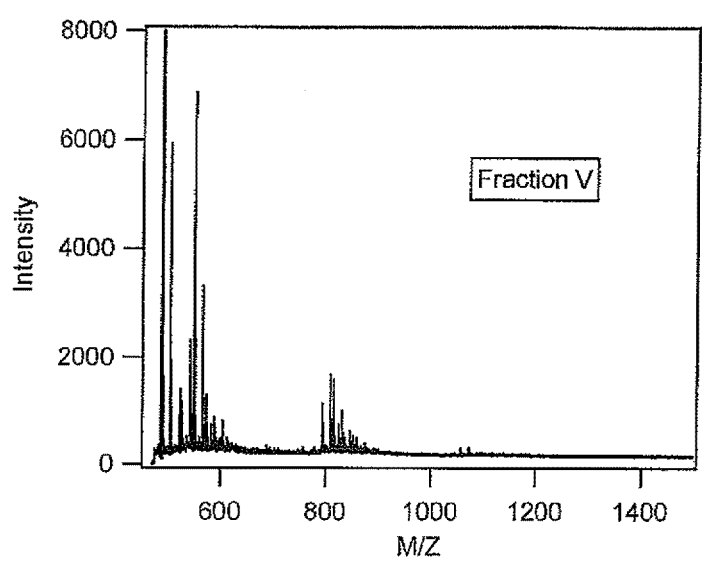
Figure 9:
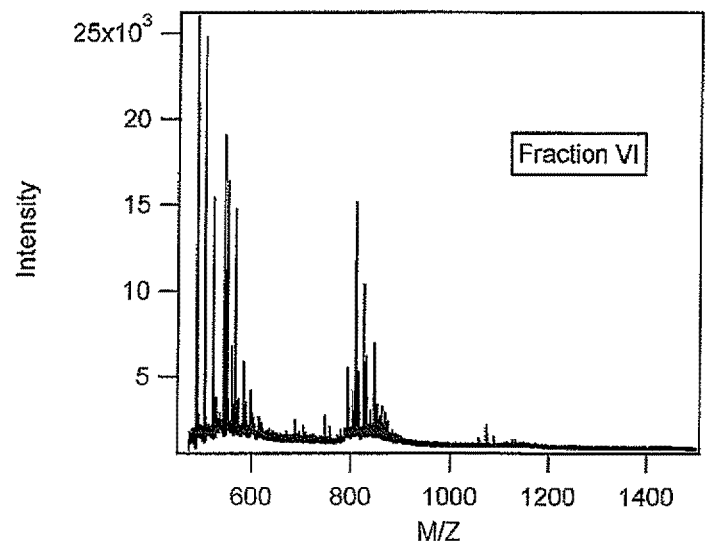
FIG. 9 shows MALDI-TOF spectra for fractions VI and VII.
Figure 9:
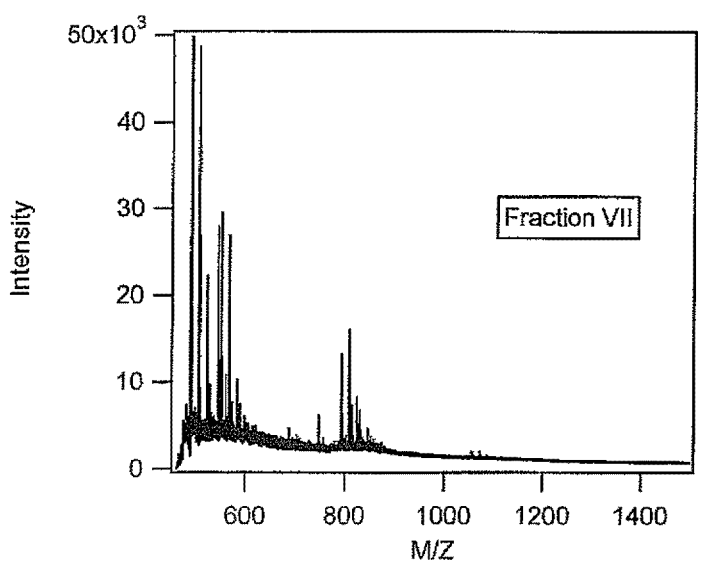

Referring now to FIG. 1, a resorcinol polyepicatechin having seven fractions is prepared using, for example, the process described in Bruno et al, U.S. Patent Publication No. 2009/0170928 and separated using HPLC. It has been found that each of the seven fractions are reflected as various peaks in the chromatogram shown in FIG. 1. In particular, fraction 1, fraction 2, fraction 3, fraction 4, fraction 5, fraction 6 and fraction 7 are shown.

In the present invention, the preferred polyflavonoids are those based on resorcinol polyepicatechin and fractions based on resorcinol polyepicatechin separated via HPLC. The separated fractions are the fourth ($4^{th}$), fifth ($5^{th}$), sixth ($6^{th}$) and seventh (7th) fractions of the polyflavonoid and are useful antioxidants for food products in a wide variety of industrial, medical, food, electronic and optical applications.

This invention is a significant advancement over current strategies used for the analysis or separation of a water soluble and processable form of synthetic polyflavonoids. The present invention addresses and resolves all of the current limitations which have prevented the commercial viability and use of enzymatically prepared poly/oligoflavonoids. The fraction utilized in this disclosure provides a specific antioxidant that can be utilized in food or in the drug industry. In addition, the fraction obtained from the HPLC separation can be redissolved in ethanol to obtain a high purity fraction, and may be easily redissolved in water. This is a significant advancement for the development of new phenolic polymers with enhanced purity and high specific antioxidant properties. When used in an application based on antioxidant properties, the fraction can be used in amounts of from 1 part per billion (ppb) to 100 ppb.

As used herein, a "flavonoid" includes naturally occurring phenols that are commonly termed flavonoids and unnatural isomers or optionally substituted variations thereof. For example, flavonoids can be selected from optionally substituted catechin, quercitin, flavonone, isoflavone, chalcone, anthocyanidin, chrysin, primuletin, fisetin, naringin, hesperidin, prunin, daidzein, genistein, pelargonidin, cyaniding, delphinidin, or the like.

In various embodiments, the flavonoid is selected from (−)-catechin, (−)-epicatechin, (−)-gallocatechin, (−)-catechin gallate, (−)-epigallocatechin, (−)-gallocatechin gallate, (−)-epicatechin gallate, (−)-epigallocatechin gallate, (+)-catechin, (+)-epicatechin, (+)-gallocatechin, (+)-catechin gallate, (+)-epigallocatechin, (+)-gallocatechin gallate, (+)-epicatechin gallate, and (+)-epigallocatechin gallate, whereby the oligo/polyflavanoid synthesized can be oligo/poly(−)-catechin, oligo/poly(−)-epicatechin, oligo/poly(−)-gallocatechin, oligo/poly(−)-catechin gallate, oligo/poly(−)-epigallocatechin, oligo/poly(−)-gallocatechin gallate, oligo/poly(−)-epicatechin gallate, oligo/poly(−)-epigallocatechin gallate, oligo/poly(+)-catechin, oligo/poly(+)-epicatechin, oligo/poly(+)-gallocatechin, oligo/poly(+)-catechin gallate, oligo/poly(+)-epigallocatechin, oligo/poly(+)-gallocatechin gallate, oligo/poly(+)-epicatechin gallate, or oligo/poly(+)-epigallocatechin gallate.

In various embodiments, the biocompatible polymerization solubilizer can include a mixed solvent selected from water-ethanol, water-dimethyl sulfoxide, water-isopropyl alcohol, additional polymerization solubilizers include water-dimethyl formamide. In certain embodiments the biocompatible solubilizer is a mixed solvent selected from water-ethanol, water-dimethyl sulfoxide and water-isopropyl alcohol.

In certain embodiments the biocompatible solubilizer is a mixed solvent selected from water-ethanol, and water-isopropyl alcohol. In certain embodiments the biocompatible solubilizer is a mixed solvent of water-ethanol. The mixed solvents can be in a ratio of water:organic solvent from about 1:99 to about 99:1, or in some embodiments, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5, or in particular embodiments, water:organic solvent in a ratio of about 90:10. In particular embodiments, the biocompatible polymerization solubilizer can be a water-ethanol mixture with up to 20% of ethanol.

In typical embodiments, the polymerization agent includes an oxido-reductase. Examples of oxido-reductases can include horseradish peroxidase (HRP) soybean peroxidase (SBP), lignin peroxidase (UP), managanese peroxidase (MnP), laccases, or the like. In particular embodiments, the polymerization agent can be HRP in combination with hydrogen peroxide.

Preferred enzymes used for the polymerization are HRP, laccase (used with bubbled air or oxygen) and pegylated hemadine.

The polymerization is preferably carried out at temperatures of about 20 to 37° C. at ratios of about 0.5 to 2.3 mg of flavonoid to 0.4 mg of enzyme, preferably HRP, at flavonoid concentrations of about 0.4 to 2 mg/ml of $H_2O$ at a pH of from about 4.3 to 7.9.

The polyflavonoids may include, but are not limited to, various substituent groups at the ortho and meta positions to sterically control the orientation of the monomers with respect to the polyelectrolyte matrix during the polymerization. Suitable functional groups include, but are not limited to, methoxy, methyl, ethyl, sulfonate, carboxylate and hydroxyl groups which are preferably in the ortho position of the resorcinol or catechol.

The matrix materials that can be used to increase the solubility of the final polymer may include but are not limited to, polyelectrolytes or surfactants for micelle formation or electrolytes which have various aromatic backbones and/or pendant groups, aliphatic backbones and/or pendant groups, optically active (chromophoric) backbones and/or pendant groups, electrically active backbones and/or pendant groups and various degrees of ionization.

The ionized groups on these matrix materials may include but are not limited to sulfonates, carboxylates, and phosphates chondroitin keratan and dermatan. The matrix may also contain the appropriate functional groups such that they can interact with the monomers through hydrogen bonding type of interactions.

Manipulation of the molecular weight, purity and charge of the matrices will allow for optimized polymerization and processing conditions.

The functionalities of the polymers may be tuned to impart the required mechanical, thermal, chemical, medical, electrical and optical properties through copolymerization with other functionalized monomers. A carboxylic acid, amine or sugar may be added to alter acidity or increase solubility.

The polymers, to be separated, have sites for further modifications including but not limited to covalently coupling other functionalities, thermal and UV crosslinkers and even biomolecules through simple coupling chemistry.

The polyflavonoid in the resulting polymer complexes will allow for use in a wide range of applications including, but not limited to, wood composites laminates, foundry resins, abrasives, friction and molding materials, coatings and adhesives, fiber bonders and flame retardants, smart windows, chaff materials, food antioxidant, drugs for various health issues such as cancer and drug delivery systems Accordingly, to achieve the foregoing objects and in accordance with the purpose of the invention, as embodied and broadly described herein, a method for the separation of enzyme-catalyzed polymerized flavonoid such as catechins or epicatechins comprises the separation of an aqueous solution containing a polyflavonoid into two or more fractions. The resulting polymer fractions in solution can be immediately used as is for subsequent processing strategies subject to removal of solvents. The solvents can be removed by routine techniques known to those of skill in the art and include solvent evaporation. Alternatively, the separated fraction(s) can be used in a powdered form. The described methods, particularly the testing of the enzymatic polyflavonoid by using polyamide oxidative fluorescence, results in a highly active oil antioxidant.

In a preferred embodiment, the separation is carried out using HPLC techniques at temperatures from about ambient to 60° C., particularly from about 35° C. to 60° C. wherein the mobile phase is an organic solvent/water mixture with a concentration gradient of the organic solvent as a function of time.

The preferred organic solvent is acetonitrile. The method of the present invention results in recovery of highly pure fractions.

The method of the invention, particularly the separation of the enzymatic polyflavonoid by using the specified gradient and automated fraction collector provides good results. In a preferred embodiment, the column is a phenyl column. A Zorbax Eclipse XDB pheny column is an example of a suitable column.

For the separation, an HPLC system, such as an Agilent 1200 Series LC system comprising an Agilent 1315B diode array detector (DAD) binary pump, vacuum degasser, autosampler, thermostatted column compartment and fraction collector can be used. The mobile phase can be an organic solvent/water mixture, preferably an acetonitrile mixture. The column temperature is preferably about 35° C., but the separation can be conducted at all temperatures between ambient and 60° C. with slightly different retention times.

FTIR, Circular Voltammetry (CV) and optical measurements shown in FIGS. 2 to 7 are consistent with structurally different pure fractions of polyflavonoid. The FTIR, MALDI-TOF (Matrix Assisted Laser Desorption/Ionization-Time of Flight) mass spectrometer and UV-Vis spectrums of each correlating fraction can be found in the Figures.

All UV-Vis spectra were obtained using a Perkin-Elmer Lambda 9 UV-Vis near-IR spectrophotometer. A Thermo Nicolet Avater 370 FT-IR spectrometer was used to obtain the FTIR spectra in the form of KBr pellets or by casting a film on a ZnSe substrate.

The impetus behind the novel separation approach described in this invention is the use of a separated and/or pure polyflavonoid fraction. Since polyflavonoids prepared using prior art enzymatic strategies are difficult to purify without using harsh, chemical modification or involved synthetic strategies, this new approach provides a significant improvement in mild separation conditions, and inexpensive separation opportunities for commercial applications.

The polyflavonoids prepared using prior art enzymatic strategies result in an unpurified mixture without a specific antioxidant behavior. Nevertheless, the isolated fractions provide significant improvement in retarding or inhibiting oxidation as demonstrated by mild oil antioxidant testing and thus provide opportunities for commercial applications.

EXAMPLE 1

40.00 µL of polyepicatechin synthesized with horseradish peroxidase were injected in a Zorbax Eclipse XDB-phenyl Rapid Resolution column, 4.6×150 mm, 3.5 µm. The packing contained a dimethyl-phenethylsilane bonded to ultra high pure silica support ($\geq$99.995% $SiO_2$). The spherical particles in the column had a surface area of 180 $m^2$/g and a controlled pore size of 80 Å. The flow rate was 1.00 mL/min, with a gradient run of acetonitrile/water: 4.0% acetonitrile at time 0, 8.0% at 0.7 minutes, 9.0% at 1.6 minutes, 12.0% at 2.0 minutes, held for 1-minute, 15.0% at 3.5 minutes, 16.0% at 4.0 minutes, 18.5% at 4.5 minutes, 20.0% at 7.5 minutes, 80.0% at 13.5 minutes and 95.0% at 14 minutes, held for 5 minutes. The DAD was set at a signal of 380 nm, a bandwidth of 16 and a slit of 4 nm. The column temperature was maintained at a temperature of 35° C. The pH was neutral. The automated injector was set for a 40.00 µL at a draw speed and eject speed of 100.00 µL. Seven (7) fractions of polyflavonoid were separated and collected.

Furthermore, the separation can be applied to polymers such as polyepicatechin templated with polyelectrolytes (such as polystyrene sulfonate, polyethylene oxide etc), polycatechin (+, −, ±), polyquercetin, polyresveratrol, polyrutin, copolymers of flavonoids, phenolic antioxidant such as hydroxytyrosol etc

EXAMPLE 2

The oxidation of flaxseed oil and evaluation of antioxidants was measured using a method adapted from Porter, W. L.; E. D. Black; A. M. Drolet. Use of Polyamide Oxidative Fluorescence Test on Lipid Emulsions: Contrast in Relative Effectiveness of Antioxidants in Bulk Versus Dispersed Systems. J. Agric. Food Chem. 1989. 37, 615-624.

Briefly, bulk, dry flaxseed oil is oxidized using prooxidant cobalt and heat as accelerants, volatile oxidation by-products are captured on polyamide TLC plates, and the plates monitored for changes in fluorescent intensity. Method details are described below.

Enzymatically polymerized flavonoids were fractionated via HPLC using the above described method. The HPLC apparatus used therein included a Zorbax Eclipse XDB-phenyl column and employed an organic solvent (such as acetonitrile) aqueous mobile phase with a variable concentration of the organic solvent. The recovered fractions were subjected to oil oxidation experiments in an 80:20 water:ethanol solvent mix. Using the starting concentration of flavonoid monomer and solvent from enzymatic polymerization, HPLC inject volume, HPLC flow rate, and HPLC peak area %, the oil oxidation test concentrations of fractions in the bulk oil experiments was calculated to be: fraction 4 (F4)=14 ppb, F5=10 ppb, F6=5 ppb, and F7=5 ppb.

Flaxseed oil preparation for fluorescent assessment using prooxidant cobalt and heat as accelerants was as follows: 13 g of Barleans organic, unfiltered, flaxseed oil (Ferndale, Wash.) was weighed into a 50 ml centrifuge tube, and vortexed with 600 ul of fraction or epicatechin monomer in water:ethanol solvent. Flaxseed oil composition is 7.43% saturated fat, 57.21% omega-3, 16.64% omega-6, and 18.72% omega-9. Cobalt (II) chloride hexahydrate (Sigma-Aldrich, C8661; St Louis, Mo.) was milled to a powder using mortar, and added to the oil/antioxidant mix at 5 mg/g and experiment set at time zero. The cobalt was dispersed into the oil using a Fisher Scientific Tissuemiser on speed 4 (20,000 rpm) for 1 minute. The activated oil (4 ml) was then dispensed into three Pyrex glass Petri dishes using a 1000 µl Drummond plunger pipette 1 ml at a time with constant stirring to minimize cobalt settling out of oil.

Polyamide-coated terephthalate plastic plates (Polygram Polyamid-6; Macherey-Nagel, GmbH) were attached powder side down by double-sided transparent tape to the undersurface of the Petri plate lid. The polyamide plates, 2 cm×3 cm were cut from 20 cm×20 cm standard plates used for thin-layer chromatography. They contain a fluorophore (zinc silicate) activated by short wave UV but are not active in the 392 nm range used here.

The covered Petri dishes containing oil, with attached polyamide plates, were placed into a 60° C. draft oven. They were sampled at 30 minute intervals by removing the dish to a room temperature bench, immediately substituting the polyamide Petri lid with a blank Petri lid, and measuring accumulated fluorescent lipid oxidation by-products captured on the polyamide plate.

Fluorescent measurements of the polyamide plates was accomplished using Horiba Jobin Yvon FluoroLog-3 (Edison, N.J.) fluorescence spectrophotometer with solid sample adapter attached set at 60° off center. Using the spectrofluorometer front-face fluorescent setting, the excitation wavelength was set at 392 nm, the scanning emission was set 400-500 nm in 1 nm increments, slit width excite at 0.65 nm, slit width emission 0.65 nm. The increase in fluorescent counts per second (cps) was monitored at emission wavelength 450-460 nm.

Figure 10:
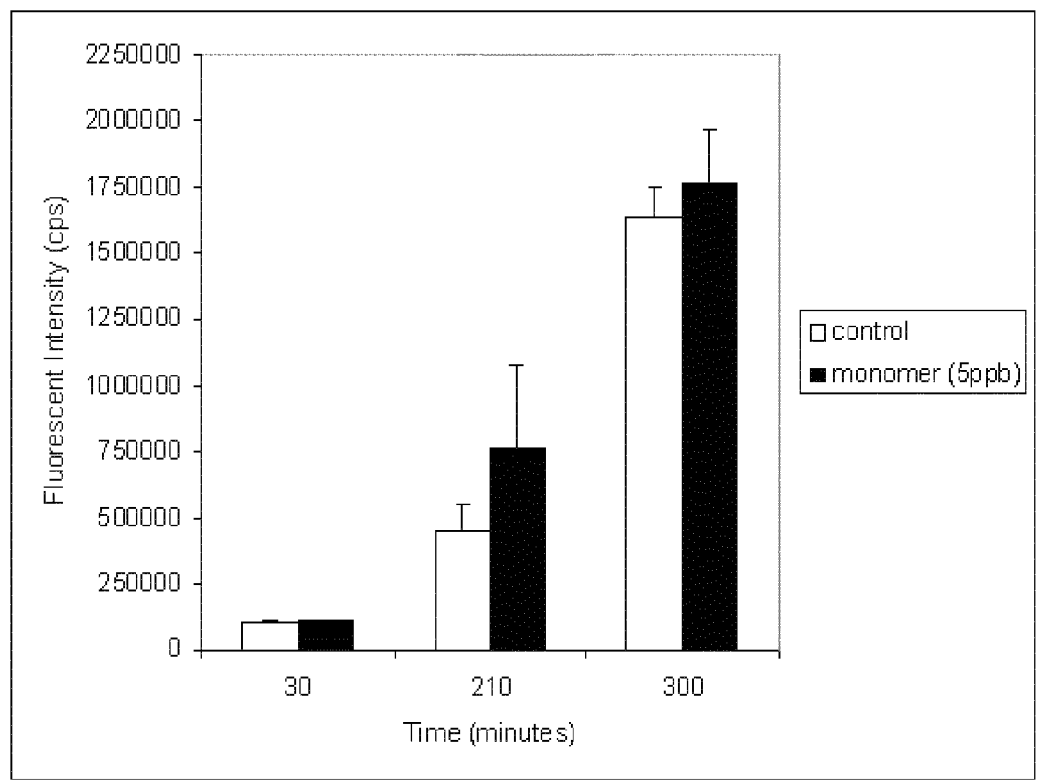
FIG. 10 shows the effect of epicatechin monomer on the inhibition of flax oil oxidation.

The flaxseed oil was tested against the epicatechin monomer (Sigma-Aldrich, Wi) used for the polymerization experiment. FIG. 10 shows the effect of epicatechin monomer on the inhibition of flaxseed oil oxidation. As shown no significant difference from the control was found at 30, 210, or 300 minutes. The results were analyzed using the Students t-test. The shown values are mean+/−SD (n=3) P<0.05.

At very low concentration (5 ppb) tested here, the monomer epicatechin has no significant inhibition on the initiation and development of flaxseed oil oxidation by-products versus a control.

Figure 11:
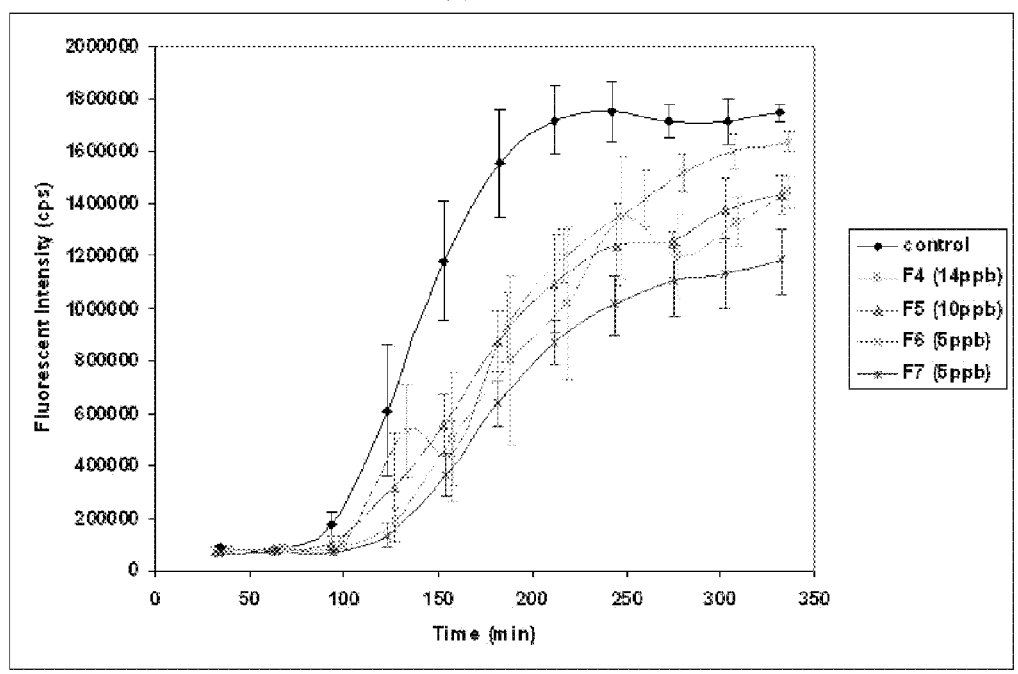
FIG. 11 show the effect of HPLC fractions of polymerized epicatechin on the inhibition of flaxseed oil oxidation.
Figure 12:
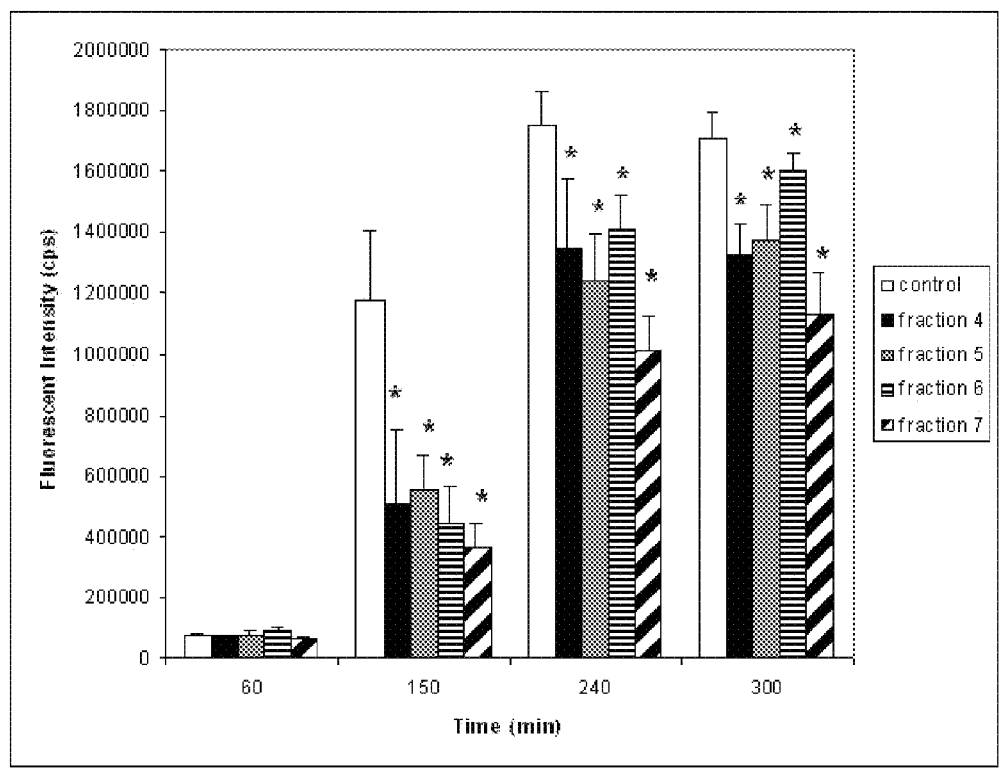
FIG. 12 shows the effect of HPLC fractions of polymerized epicatechin on the inhibition of flaxseed oil oxidation.

HPLC fractions of polymerized epicatechin were then tested in a separate but otherwise identical experiment on the ability to inhibit oxidation of flaxseed oil. The inhibition of flaxseed oil oxidation by the HPLC fractions of enzymatically polymerized epicatechin is shown in FIG. 11. In FIG. 11, F4=fraction 4, F5=fraction 5, F6=fraction 6, and F7=fraction 7. Values are mean+/−SD (n=3). All fractions appear to delay slightly the induction time the time of initiation of oxidation by-products. Once initiated, the rate of oxidation appears inhibited (lower slope of oxidation curve after initiation) in all fractions. However, maximum fluorescent intensity of the by-products is not reached to that level of control in any fraction (except possibly fraction 6). In particular, fraction 7 appears to have a) longest induction time b) lowest rate of oxidation once initiated, and c) lowest oxidation by-product maximum among all fractions. This is more closely illustrated in FIG. 12 where F4=fraction 4, F5=fraction 5, F6=fraction 6, and F7=fraction 7. Again, the values are mean+/−SD (n=3) using the Students t-test for mean difference from control (P<0.05).

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A repeatable method of retarding oxidation of an oxidizable, organic material comprising flaxseed oil, comprising:
adding an effective amount of an antioxidant to said oxidizable, organic material wherein the antioxidant comprises at least one separated fraction, the at least one separated fraction being obtained by a fractionation of a polyepicatechin complex from an enzymatic polymerization by the process comprising:
preparing a reaction mixture from enzymatic polymerization of a conjugated flavonoid consisting of a synthetic polyepicatichen;
introducing said reaction mixture into an HPLC column at a temperature that is in a range from about 35° C. to about 60° C. and wherein the HPLC column comprises a phenyl column;
introducing a mobile phase into said column, said mobile phase comprising an organic solvent/water mixture wherein the organic solvent consists of acetonitrile in a concentration gradient as a function of time;
increasing the organic solvent concentration of the mobile phase as a function of time via a non-linear gradient;
recovering seven subgroups from the synthesized polymers wherein each of the seven subgroups has a separate eluting fraction and each is spaced in time; and
selecting one of the eluting fractions to combine with the oxidizable, organic material.

2. The method of claim 1 wherein the amount of the antioxidant is from 1 ppb to 100 ppb of the oxidizable, organic material.

3. The method of claim 1 wherein selecting one of the eluting fractions comprises selecting the eluting fraction that is last in time to combine with the flaxseed oil.

* * * * *